US012611370B2

(12) United States Patent
Abe

(10) Patent No.: US 12,611,370 B2
(45) Date of Patent: Apr. 28, 2026

(54) MICROEMULSION COMPOSITION AND COSMETIC CONTAINING THE SAME

(71) Applicant: SHIN-ETSU CHEMICAL CO., LTD., Tokyo (JP)

(72) Inventor: Takuya Abe, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 693 days.

(21) Appl. No.: 17/919,391

(22) PCT Filed: Feb. 10, 2021

(86) PCT No.: PCT/JP2021/005086
§ 371 (c)(1),
(2) Date: Oct. 17, 2022

(87) PCT Pub. No.: WO2021/215084
PCT Pub. Date: Oct. 28, 2021

(65) Prior Publication Data
US 2023/0149290 A1 May 18, 2023

(30) Foreign Application Priority Data
Apr. 24, 2020 (JP) ................................. 2020-077156

(51) Int. Cl.
| | |
|---|---|
| A61K 8/894 | (2006.01) |
| A61K 8/06 | (2006.01) |
| A61K 8/34 | (2006.01) |
| A61K 8/58 | (2006.01) |
| A61Q 1/14 | (2006.01) |

(52) U.S. Cl.
CPC .............. *A61K 8/894* (2013.01); *A61K 8/068* (2013.01); *A61K 8/345* (2013.01); *A61K 8/585* (2013.01); *A61Q 1/14* (2013.01); *A61K 2800/262* (2013.01)

(58) Field of Classification Search
CPC .. A61K 2800/262; A61K 8/068; A61K 8/585; A61K 8/86; A61K 8/345
See application file for complete search history.

(56) References Cited

U.S. PATENT DOCUMENTS

| | | | |
|---|---|---|---|
| 5,650,146 | A | 7/1997 | Shaw |
| 2004/0136943 | A1 | 7/2004 | Tomokuni |
| 2006/0051384 | A1 | 3/2006 | Scholz et al. |
| 2012/0321576 | A1 | 12/2012 | Sugiyama et al. |
| 2014/0142016 | A1 | 5/2014 | Tomokuni et al. |
| 2014/0364394 | A1 | 12/2014 | Tamura et al. |
| 2016/0303032 | A1* | 10/2016 | Kamei .................... A61K 8/19 |
| 2018/0280261 | A1 | 10/2018 | Nioh et al. |
| 2019/0133896 | A1 | 5/2019 | Tsuji et al. |
| 2021/0137830 | A1 | 5/2021 | Zamansky et al. |

FOREIGN PATENT DOCUMENTS

| | | |
|---|---|---|
| CN | 101987069 A | 3/2011 |
| CN | 104136498 A | 11/2014 |
| CN | 107613952 A | 1/2018 |
| JP | H01-293131 A | 11/1989 |
| JP | H08-508265 A | 9/1996 |
| JP | 2004-217640 A | 8/2004 |
| JP | 2005-193134 A | 7/2005 |
| JP | 2007-15972 A | 1/2007 |
| JP | 2009-196909 A | 9/2009 |

(Continued)

OTHER PUBLICATIONS

JP-2013095713-A (Google English translation, downloaded Jul. 17, 2025) (Year: 2025).*
JP-2016013975-A (Google English translation, downloaded Jul. 17, 2025) (Year: 2025).*
Apr. 20, 2021 International Search Report issued in International Application No. PCT/JP2021/005086.
Oct. 25, 2022 International Preliminary Report on Patentability issued in International Application No. PCT/JP2021/005086.

(Continued)

*Primary Examiner* — Mark V Stevens
(74) *Attorney, Agent, or Firm* — Oliff PLC

(57) ABSTRACT

A microemulsion composition containing: (A) a polyether-modified organopolysiloxane shown in the following general formula (1) having an HLB of 8.0 or more calculated by Griffin's method; (B) a polyether-modified organopolysiloxane shown in the following general formula (7) having an HLB of 5.0 or less calculated by Griffin's method; (C) a glycerol derivative shown in the following general formula (8); (D) a polyhydric alcohol other than the (C); (E) a silicone oil having a kinematic viscosity of 20 mm²/s or less at 25° C.; and (F) water, where a ratio (A)/(B) of a mass of the (A) to a mass of the (B) satisfies 1.0 to 15.0 and the microemulsion composition has a transparent to translucent appearance at 25° C. This provides a microemulsion composition having a transparent to translucent appearance.

20 Claims, No Drawings

(56)              References Cited

FOREIGN PATENT DOCUMENTS

| | | | | |
|---|---|---|---|---|
| JP | 2010-222324 | A | | 10/2010 |
| JP | 2010-254624 | A | | 11/2010 |
| JP | 2011-178769 | A | | 9/2011 |
| JP | 2012-017305 | A | | 1/2012 |
| JP | 2013-032348 | A | | 2/2013 |
| JP | 2013095713 | A | * | 5/2013 |
| JP | 2014-224061 | A | | 12/2014 |
| JP | 2015-105255 | A | | 6/2015 |
| JP | 2016013975 | A | * | 1/2016 |
| JP | 2017-066085 | A | | 4/2017 |
| WO | 2018/008653 | A1 | | 1/2018 |
| WO | 2020/012415 | A2 | | 1/2020 |

OTHER PUBLICATIONS

Apr. 12, 2024 extended Search Report issued in European Patent Application No. 21793554.3.

An, Q. et al., "Synthesis, Characterization and Application of Polyurethane Modified Polyether Block Polysiloxane," Fine Chemicals, vol. 26, No. 3, pp. 299-303, Mar. 2009.

Grenoble, Z. et al., "Mechanisms, performance optimization and new developments in demulsification processes for oil and gas applications," Advances in Colloid and Interface Science, vol. 260, pp. 32-45, 2018.

Oct. 31, 2023 Search Report issued in Chinese Patent Application No. 202180029578.8.

Dec. 19, 2025 Office Action issued in European Patent Application No. 21793554.3.

* cited by examiner

MICROEMULSION COMPOSITION AND COSMETIC CONTAINING THE SAME

TECHNICAL FIELD

The present invention relates to: a microemulsion composition containing a silicone oil; and a cosmetic containing the same.

BACKGROUND ART

In recent years, foundations that do not easily come off due to perspiration, sebum, and so forth and mascara having a waterproof function are prevalent for the purpose of preventing make-up deterioration. These contain film formers represented by silicone resin, and are therefore difficult to remove with ordinary cleansing agents. When removing the make-up, the cleansing agent needs to be spread on the skin sufficiently and blended with the make-up. However, the spreadability of the cleansing agents tend to become heavy when the cleansing agents are blended with the make-up. Therefore, a preparation for lightening the spreadability is required. In addition, a microemulsion composition having a bicontinuous structure can achieve a cosmetic having enhanced functionality and feeling on use, and from the viewpoint that the microemulsion composition can be used conveniently with wet hands, there are many reports of applications as cleansing agents (Patent Documents 1 to 7).

Bicontinuous microemulsion compositions require the use of a large amount of surfactant compared with water-dispersion emulsions or oil-dispersion emulsions. However, since stickiness or an oily feeling originating from an activator remain when used as a cosmetic, it is preferable to reduce the amount of surfactant used in order to maintain light feeling (Patent Document 8). Alternatively, a silicone-based surfactant or an oil agent is preferably used. In Patent Document 9, a bicontinuous microemulsion composition was obtained by using a silicone-based surfactant and a silicone oil, but the amount of activator used was large, and this may cause stickiness.

A microemulsion composition containing a silicone oil can be produced by using Surfactin, which is a natural surfactant. Patent Document 10 reports an emulsified composition containing Surfactin, amino-modified silicone, and an aqueous solvent. The emulsified composition is characteristic in that the emulsified composition has a high emulsifying capacity, and a small amount of surfactant suffices. However, since the activator is anionic, a strong feeling of stickiness originating from the activator remains compared with a nonionic surfactant.

A cleansing agent having spreadability improved by using a glycerol derivative as an auxiliary agent is being considered. In Patent Documents 11 and 12, a cleansing agent whose spreadability does not become heavy is obtained by using a specific glycerol derivative, but it is necessary to use a silicone oil and an ester oil in combination as an oil agent, and there are no reported examples using only silicone oil. In Patent Document 13, a microemulsion having only silicone oil blended is obtained by using a specific glycerol derivative. However, a non-silicone-based surfactant having a high HLB (Hydrophilic-Lipophilic Balance) is essential.

CITATION LIST

Patent Literature

Patent Document 1: JP 2009-196909 A
Patent Document 2: JP 2015-105255 A

Patent Document 3: JP 2017-66085 A
Patent Document 4: JP 2004-217640 A
Patent Document 5: JP 2013-32348 A
Patent Document 6: JP 2014-224061 A
Patent Document 7: JP 2010-222324 A
Patent Document 8: JP 2011-178769 A
Patent Document 9: JP 2019-99469 A
Patent Document 10: WO 2018/008653
Patent Document 11: JP 2012-017305 A
Patent Document 12: JP 2016-013975 A
Patent Document 13: JP 2007-015972 A

SUMMARY OF INVENTION

Technical Problem

The present invention has been made in view of the above-described circumstances, and objects thereof are: to provide a microemulsion composition having a transparent to translucent appearance when a silicone oil having a kinematic viscosity of 20 mm²/s or less at 25° C. is used as an oil phase even when only a silicone-based surfactant is used; and a cosmetic containing an oil-in-water type microemulsion composition.

Solution to Problem

To achieve the object, the present invention provides a microemulsion composition comprising:

(A) a polyether-modified organopolysiloxane shown in the following general formula (1) having an HLB (Hydrophilic-Lipophilic Balance) of 8.0 or more calculated by Griffin's method,

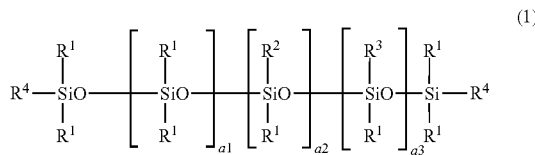

$$(1)$$

wherein $R^1$'s represent identical or different types of alkyl groups, aryl groups, or aralkyl groups having 1 to 30 carbon atoms or halogen-substituted groups, amino-substituted groups, or carboxy-substituted groups thereof, $R^2$s represent identical or different polyoxyalkylene groups shown by the following general formula (2), $$—(CH_2)_2—C_lH_{2l}O—(C_2H_4O)_b(C_3H_6O)_cR^5 \qquad (2)$$

wherein $R^5$ represents an unsubstituted or substituted monovalent hydrocarbon group or a hydrogen atom, "l", "b", and "c" are integers that satisfy $0 \leq l \leq 15$, $2 \leq b \leq 200$, $0 \leq c \leq 200$, and $3 \leq b+c \leq 200$, $R^3$s represent identical or different types of groups shown by one of the following general formulae (3) to (6), $$—(CH_2)_2—C_mH_{2m}—(SiOR^1_2)_d—SiR^1_3 \qquad (3)$$

$$—(CH_2)_2—C_mH_{2m}—SiR^1_{e1}—(OSiR^1_3)_{3-e1} \qquad (4)$$

$$—(CH_2)_2—C_mH_{2m}—SiR^1_{e1}—(OSiR^1_{e2}(OSiR^1_3)_{3-e2})_{3-e1} \qquad (5)$$

$$—(CH_2)_2—C_mH_{2m}—SiR^1_{e1}—(OSiR^1_{e2}(OSiR^1_{e3} (OSiR^1_3)_{3-e3})_{3-e2})_{3-e1} \qquad (6)$$

3 wherein $R^1$ is as described above and "m", "d", and e1 to e3 are integers that satisfy 0 m 5, $0 \leq d \leq 500$, $0 \leq e1 \leq 2$, $0 \leq e2 \leq 2$, and $0 \leq e3 \leq 2$, $R^4$s are each independently $R^1$, $R^2$, or $R^3$, a1 is a number that satisfies $0 \leq a1 \leq 100$, a2 is a number that satisfies $0 \leq a2 \leq 50$, and a3 is a number that satisfies $0 \leq a3 \leq 50$, provided that at least one $R^4$ is $R^2$ when a2 is 0;

(B) a polyether-modified organopolysiloxane shown in the following general formula (7) having an HLB of 5.0 or less calculated by Griffin's method,

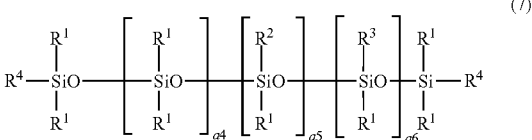

(7)

wherein $R^1$, $R^2$, $R^3$, and $R^4$ follow the above definitions, a4 is a number that satisfies $0 \leq a4 \leq 100$, a5 is a number that satisfies $0 \leq a5 \leq 50$, and a6 is a number that satisfies $0 \leq a6 \leq 50$, provided that at least one $R^4$ is $R^2$ when a5 is 0;

(C) a glycerol derivative shown in the following general formula (8), $$\text{Gly-}\{O\text{---}(PO)_f(EO)_g(BO)_hH\}_3 \qquad (8)$$

wherein Gly represents a residue in which a hydroxy group is removed from glycerol, PO represents an oxypropylene group, EO represents an oxyethylene group, "f" and "g" are respectively average numbers of moles of PO and EO added, f+g indicates a value of 1 to 30, a mass ratio of PO to EO, that is, PO/EO is 1/5 to 5/1, BO represents oxyalkylene having 4 carbon atoms, and h is an average number of moles of BO added and indicates a value of 1 to 5;

(D) a polyhydric alcohol other than the (C);

(E) a silicone oil having a kinematic viscosity of 20 mm²/s or less at 25° C.; and (F) water, wherein a ratio (A)/(B) of a mass of the (A) to a mass of the (B) satisfies 1.0 to 15.0 and the microemulsion composition has a transparent to translucent appearance at 25° C.

Such a microemulsion composition makes it possible to produce a microemulsion composition having a transparent to translucent appearance. Moreover, since a silicone-based surfactant is used as an activator and a silicone oil is used as an oil agent, the microemulsion composition has a characteristic of having little stickiness or oily feeling originating from the activator.

In this event, (A)/(B), which is the ratio of a mass of the polyether-modified organopolysiloxane (A) to a mass of the polyether-modified organopolysiloxane (B) in the microemulsion composition, is 1.0 to 15.0.

When the mass ratio is as described, a microemulsion composition that is stable and has a transparent to translucent appearance can be obtained easily.

In this event, the polyether-modified organopolysiloxane (A) preferably has an HLB of 8.0 or more and 13.0 or less calculated by Griffin's method.

Furthermore, in this event, the polyether-modified organopolysiloxane (A) more preferably has an HLB of 8.5 or more and 10.5 or less calculated by Griffin's method.

In this manner, a microemulsion composition having a transparent to translucent appearance can be obtained easily. In particular, when the HLB is 8.5 or more and 10.5 or less, a microemulsion composition having a transparent appearance can be obtained easily.

In this event, the polyether-modified organopolysiloxane (A) is preferably what is called PEG-9 Dimethicone in Cosmetic-Info.jp.

Raw materials of such a polyether-modified organopolysiloxane is readily available, and a microemulsion composition can be obtained more easily.

In this event, the microemulsion composition is preferably dispersible when added in water.

Such a microemulsion composition can be used suitably for use in cosmetics and so forth.

In this event, 0.1 to 10 wt % of the polyether-modified organopolysiloxane (A) is preferably contained relative to the microemulsion composition.

When the polyether-modified organopolysiloxane (A) is within the above range, a D phase is easily formed.

In this event, the polyhydric alcohol (D) is preferably glycerol or a glycerol derivative.

In this manner, a D phase can be formed in a wide concentration range.

In this event, the (E) is preferably one or more selected from decamethylcyclopentasiloxane, dimethyl polysiloxane, and methylphenylpolysiloxane.

Such a silicone oil is a volatile silicone oil having a boiling point of 260° C. or lower under one atmospheric pressure, and can be used suitably in the inventive microemulsion composition.

In addition, the present invention can provide a cosmetic comprising the above-described microemulsion composition.

When a cosmetic is thus prepared using the above-described microemulsion composition as a base, a cosmetic having excellent spreadability on application, a refreshing feeling, a high cleansing effect, and excellent cleaning performance and stability over time is achieved.

Advantageous Effects of Invention

As described above, the inventive microemulsion composition combines a specific glycerol derivative and polyhydric alcohol at a specific proportion and uses two types of polyether-modified organopolysiloxanes having different HLBs as surfactants. Thus, it is possible to produce a microemulsion composition having a transparent to translucent appearance without necessarily using an anionic or cationic surfactant when a silicone oil having a kinematic viscosity of 20 mm²/s or less at 25° C. is used as the oil phase. A cleansing cosmetic containing the microemulsion composition has excellent spreadability on application, a refreshing feeling, a high cleansing effect, and excellent cleaning performance.

DESCRIPTION OF EMBODIMENTS

Hereinafter, the present invention will be described in detail, but the present invention is not limited thereto.

As described above, it has been desired: to provide a microemulsion composition having a transparent to translucent appearance when a silicone oil having a kinematic viscosity of 20 mm²/s or less at 25° C. is used as an oil phase even when no anionic or cationic surfactants is used and only a silicone-based surfactant is used; and to develop a cosmetic containing an oil-in-water type microemulsion composition.

To achieve the object, the present inventor has earnestly studied and found out that by combining a specific glycerol derivative and polyhydric alcohol and by using two types of polyether-modified organopolysiloxanes having different HLBs as surfactants, a microemulsion composition that has a transparent to translucent appearance and is thermodynamically stable can be obtained when a silicone oil having a kinematic viscosity of 20 mm²/s or less at 25° C. is used as the oil phase.

In addition, the present inventor has observed that it is possible to obtain a cleansing agent that has excellent spreadability on application, a refreshing feeling, a high cleansing effect, and excellent cleaning performance, and arrived at the present invention.

That is, the present invention is a microemulsion composition comprising:

(A) a polyether-modified organopolysiloxane shown in the following general formula (1) having an HLB (Hydrophilic-Lipophilic Balance) of 8.0 or more calculated by Griffin's method,

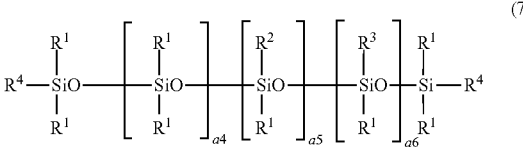

(1)

wherein $R^1$s represent identical or different types of alkyl groups, aryl groups, or aralkyl groups having 1 to 30 carbon atoms or halogen-substituted groups, amino-substituted groups, or carboxy-substituted groups thereof, $R^2$s represent identical or different polyoxyalkylene groups shown by the following general formula (2), $$—(CH_2)_2—C_lH_{2l}—O—(C_2H_4O)_b(C_3H_6O)_cR^5 \quad (2)$$

wherein $R^5$ represents an unsubstituted or substituted monovalent hydrocarbon group or a hydrogen atom, "l", "b", and "c" are integers that satisfy $0 \leq l \leq 15$, $2 \leq b \leq 200$, $0 \leq c \leq 200$, and $3 \leq b+c \leq 200$, $R^3$s represent identical or different types of groups shown by one of the following general formulae (3) to (6), $$—(CH_2)_2—C_mH_{2m}—(SiOR^1_2)_d—SiR^{13} \quad (3)$$

$$—(CH_2)_2—C_mH_{2m}—SiR^1_{e1}—(OSiR^1_3)_{3-e1} \quad (4)$$

$$—(CH_2)_2—C_mH_{2m}—SiR^1_{e1}—(OSiR^1_{e2} \\ (OSiR^1_3)_{3-e2})_{3-e1} \quad (5)$$

$$—(CH_2)_2—C_mH_{2m}—SiR^1_{e1}—(OSiR^1_{e2}(OSiR^1_{e3} \\ (OSiR^1_{e3})_{3-e3})_{3-e2})_{3-e1} \quad (6)$$

wherein $R^1$ is as described above and "m", "d", and e1 to e3 are integers that satisfy $0 \leq m \leq 5$, $0 \leq d \leq 500$, $0 \leq e1 \leq 2$, $0 \leq e2 \leq 2$, and $0 \leq e3 \leq 2$, $R^4$s are each independently $R^1$, $R^2$, or $R^3$, a1 is a number that satisfies $0 \leq a1 \leq 100$, a2 is a number that satisfies $0 \leq a2 \leq 50$, and a3 is a number that satisfies $0 \leq a3 \leq 50$, provided that at least one $R^4$ is $R^2$ when a2 is 0;

(B) a polyether-modified organopolysiloxane shown in the following general formula (7) having an HLB of 5.0 or less calculated by Griffin's method,

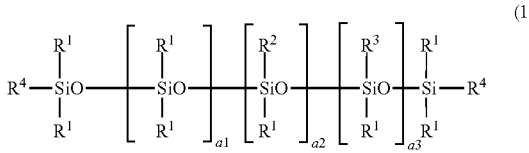

(7)

wherein $R^1$, $R^2$, $R^3$, and $R^4$ follow the above definitions, a4 is a number that satisfies $0 \leq a4 \leq 100$, a5 is a number that satisfies $0 \leq a5 \leq 50$, and a6 is a number that satisfies $0 \leq a6 \leq 50$, provided that at least one $R^4$ is $R^2$ when a5 is 0;

(C) a glycerol derivative shown in the following general formula (8), $$Gly-\{O—(PO)_f(EO)_g(BO)_hH\}_3 \quad (8)$$

wherein Gly represents a residue in which a hydroxy group is removed from glycerol, PO represents an oxypropylene group, EO represents an oxyethylene group, "f" and "g" are respectively average numbers of moles of PO and EO added, f+g indicates a value of 1 to 30, a mass ratio of PO to EO, that is, PO/EO is 1/5 to 5/1, BO represents oxyalkylene having 4 carbon atoms, and h is an average number of moles of BO added and indicates a value of 1 to 5;

(D) a polyhydric alcohol other than the (C);

(E) a silicone oil having a kinematic viscosity of 20 mm²/s or less at 25° C.; and (F) water, wherein a ratio (A)/(B) of a mass of the (A) to a mass of the (B) satisfies 1.0 to 15.0 and the microemulsion composition has a transparent to translucent appearance at 25° C.

[Component A]

The polyether-modified organopolysiloxane (A) having an HLB of 8.0 or more calculated by Griffin's method used in the present invention is shown by the following general formula (1).

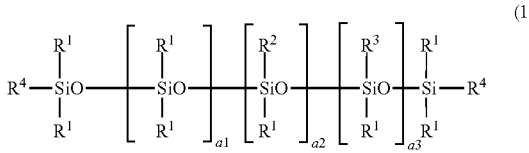

(1)

In the formula, $R^1$s represent identical or different types of alkyl groups, aryl groups, or aralkyl groups having 1 to 30 carbon atoms or halogen-substituted groups, amino-substituted groups, or carboxy-substituted groups thereof. In particular, alkyl groups, aryl groups, aralkyl groups, fluorine-substituted alkyl groups, chloro-substituted alkyl groups, amino-substituted alkyl groups, and carboxyl-substituted alkyl groups having 1 to 10 carbon atoms are preferable. More specific examples include a methyl group, an ethyl group, a propyl group, a butyl group, a pentyl group, a cyclopentyl group, a cyclohexyl group, a phenyl group, a tolyl group, etc., a trifluoropropyl group, a heptadecafluorodecyl group, a chloropropyl group, a chlorophenyl group, and the like. An alkyl group having 1 to 5 carbon atoms, a phenyl group, or a trifluoropropyl group is further preferable.

$R^2$s represent identical or different polyoxyalkylene groups shown by the following general formula (2).

$$—(CH_2)_2—C_lH_{2l}—O—(C_2H_4O)_b(C_3H_6O)_cR^5 \tag{2}$$

In the formula, $R^5$ represents an unsubstituted or substituted monovalent hydrocarbon group or a hydrogen atom, and "l", "b", and "c" are integers that satisfy $0 \le l \le 15$, $2 \le b \le 200$, $0 \le c \le 200$, and $3 \le b+c \le 200$.

In the above formula, $R^5$ represents an unsubstituted or substituted monovalent hydrocarbon group or a hydrogen atom. "l" is $0 \le l \le 15$, preferably $0 \le l \le 2$. "b" is $2 \le b \le 200$, preferably 2≤b 100, and further preferably $2 \le b \le 50$. If "b" is greater than 200, hydrophilicity becomes too high, and so that stability is lost. "c" is $0 \le c \le 200$, preferably $0 \le c \le 100$, and further preferably $0 \le c \le 50$. If "c" is greater than 200, hydrophilicity becomes too high, so that stability is lost. b+c is $3 \le b+c \le 200$, preferably $3 \le b+c \le 100$, further preferably $3 \le b+c \le 50$. If b+c is smaller than 3, hydrophilicity becomes poor, so that emulsifying property is weakened and stability is lost. In order to provide sufficient hydrophilicity for obtaining a water-in-oil type emulsion, $b/c \ge 1$ is desirable, and in order to provide sufficient hydrophobicity for obtaining an oil-in-water type emulsion, $b/c \le 1$ is desirable. When a polyoxyalkylene moiety includes both an ethyleneoxide unit and a propyleneoxide unit, either a block copolymer or a random copolymer of these two units is possible.

$R^3$s represent identical or different types of groups shown by one of the following general formulae (3) to (6).

$$—(CH_2)_2—C_mH_{2m}—(SiOR^1_2)_d—SiR^{13} \tag{3}$$

$$—(CH_2)_2—C_mH_{2m}—SiR^1_{e1}—(OSiR^1_3)_{3-e1} \tag{4}$$

$$—(CH_2)_2—C_mH_{2m}—SiR^1_{e1}—(OSiR^1_{e2}(OSiR^1_3)_{3-e2})_{3-e1} \tag{5}$$

$$—(CH_2)_2—C_mH_{2m}—SiR^1_{e1}—(OSiR^1_{e2}(OSiR^1_{e3}(OSiR^1_3)_{3-e3})_{3-e2})_{3-e1} \tag{6}$$

In the formulae, $R^1$ is as described above, and "m", "d" and e1 to 3 are integers that satisfy $0 \le m \le 5$, $0 \le d \le 500$, $0 \le e1 \le 2$, $0 \le e2 \le 2$, and $0 \le e3 \le 2$.

Examples and suitable ranges of $R^1$ in these general formulae are as described above, and "m" is $0 \le m \le 5$, preferably $0 \le m \le 2$, "d" is $0 \le d \le 500$, preferably $1 \le d \le 100$, more preferably 1 d 50. If "d" is greater than 500, hydrophilicity becomes poor, so that stability is lost.

$R^4$s are each independently $R^1$, $R^2$, or $R^3$. In addition, a1 is $0 \le a1 \le 100$, preferably $1 \le a1 \le 50$, and further preferably $1 \le a1 \le 30$. If a1 is greater than 100, hydrophilicity becomes poor, so that it is difficult to obtain a stable emulsion. a2 is $0 \le a2 \le 50$, preferably $1 \le a2 \le 30$, and further preferably 1 K a2≤10. If a2 is greater than 50, hydrophilicity becomes too high, so that stability is lost. a3 is $0 \le a3 \le 50$, preferably $0 \le a3 \le 30$, and further preferably $0 \le a3 \le 10$. If a3 is greater than 50, hydrophilicity becomes poor, so that stability is similarly lost. Here, at least one $R^4$ is $R^2$ when a2 is 0.

When regarded as an emulsifier, the weight-average molecular weight of the polyether-modified organopolysiloxane shown by the general formula (1) is not particularly limited, but is preferably 500 to 200,000, particularly preferably 1,000 to 100,000.

The polyether-modified organopolysiloxane shown by the general formula (1) of the present invention can be synthesized easily by subjecting an organohydrogenpolysiloxane, a polyoxyalkylene compound shown by the following general formula (2'), a silicone compound shown by one of the following general formulae (3') to (6'), and furthermore, in some cases, a terminal unsaturated group-containing alkylene compound to addition reaction in the presence of a platinum catalyst or a rhodium catalyst. Here, the organohydrogenpolysiloxane may be either linear or cyclic, but in view of carrying out the addition reaction smoothly, the organohydrogenpolysiloxane is preferably mainly linear.

$$\diagup\!\diagup C_lH_{2l}—O——(C_2H_4O)_b(C_3H_6O)_cR^5 \tag{2'}$$

In the formula, $R^5$, "l", "b", and "c" are as described above.

$$\diagup\!\diagup C_mH_{2m}—(SiOR^1_2)_d—SiR^1_3 \tag{3'}$$

$$\diagup\!\diagup C_mH_{2m}—SiR^1_{e1}—(OSiR^1_3)_{3-e1} \tag{4'}$$

$$\diagup\!\diagup C_mH_{2m}—SiR^1_{e1}—(OSiR^1_{e2}(OSiR^1_3)_{3-e2})_{3-e1} \tag{5'}$$

$$\diagup\!\diagup C_mH_{2m}—SiR^1_{e1}—(OSiR^1_{e2}(OSiR^1_{e3}(OSiR^1_3)_{3-e3})_{3-e2})_{3-e1} \tag{6'}$$

In the formulae, $R^1$, "m", "d", and e1 to e3 are as described above.

The mixing ratio of the organohydrogenpolysiloxane to the total of the polyoxyalkylene compound shown by the general formula (2'), the silicone compound shown by one of the general formulae (3') to (6'), and the terminal unsaturated group-containing alkylene compound is, for example, as follows: the molar ratio of the terminal unsaturated group is 0.5 to 2.0, preferably 0.8 to 1.2 relative to 1 mol of SiH groups.

Furthermore, the addition reaction is preferably performed in the presence of a platinum catalyst or a rhodium catalyst. Specifically, catalysts such as a chloroplatinic acid, an alcohol-modified chloroplatinic acid, a chloroplatinic acid-vinylsiloxane complex, etc. are suitably used. Note that the amount of the catalyst to be used can be a catalytic amount, and in particular, the amount of platinum or rhodium is 50 ppm or less, preferably 20 ppm or less.

The above-described addition reaction may be performed in an organic solvent as necessary. Examples of the organic solvent include aliphatic alcohols such as methanol, ethanol, 2-propanol, and butanol; aromatic hydrocarbons such as toluene and xylene; aliphatic or alicyclic hydrocarbons such as n-pentane, n-hexane, and cyclohexane; halogenated hydrocarbons such as dichloromethane, chloroform, and carbon tetrachloride; and the like. In particular, for use in cosmetics, ethanol and 2-propanol (isopropyl alcohol) are suitable. Addition reaction conditions are not particularly limited, but it is suitable to perform the reaction under reflux for 1 to 10 hours.

The polyether-modified organopolysiloxane (A) has an HLB of 8.0 or more calculated by Griffin's method. Griffin's method is defined as: "value of HLB"=20×(the sum total of the molecular weight of hydrophilic moieties/total molecular weight). In addition, an HLB value is a numerical value that signifies the affinity of a surfactant with water and oil agents. If HLB goes below 8.0, there is a possibility of the appearance of the obtained microemulsion composition being degraded.

In this event, the polyether-modified organopolysiloxane (A) preferably has an HLB of 8.0 or more and 13.0 or less calculated by Griffin's method. In this manner, a microemulsion composition having a transparent to translucent appearance can be obtained easily.

Furthermore, in this event, the polyether-modified organopolysiloxane (A) more preferably has an HLB of 8.5 or more and 10.5 or less calculated by Griffin's method. In this manner, a microemulsion composition having a transparent appearance can be obtained easily.

Furthermore, the polyether-modified organopolysiloxane (A) having the HLB of 8.5 or more and 10.5 or less calculated by Griffin's method is desirably PEG-9 Dimethicone in Cosmetic-Info.jp. Such a substance is not limited to the following example, but for example, "KF-6013" manufactured by Shin-Etsu Chemical Co., Ltd. can be used. When such a polyether-modified organopolysiloxane is used, raw materials can be easily obtained, and a microemulsion composition can be obtained more easily.

[Component B]

The polyether-modified organopolysiloxane having an HLB of 5.0 or less calculated by Griffin's method, the polyether-modified organopolysiloxane being the component (B) used in the present invention, is shown by the following general formula (7).

$$
R^4\!-\!\underset{\underset{R^1}{|}}{\overset{\overset{R^1}{|}}{Si}}O\!-\!\left[\underset{\underset{R^1}{|}}{\overset{\overset{R^1}{|}}{Si}}O\right]_{a4}\!\!\left[\underset{\underset{R^1}{|}}{\overset{\overset{R^2}{|}}{Si}}O\right]_{a5}\!\!\left[\underset{\underset{R^1}{|}}{\overset{\overset{R^3}{|}}{Si}}O\right]_{a6}\!\!\underset{\underset{R^1}{|}}{\overset{\overset{R^1}{|}}{Si}}\!-\!R^4 \tag{7}
$$

In the formula, $R^1$, $R^2$, $R^3$, and $R^4$ follow the above definitions. a4 is a number that satisfies $0 \leq a4 \leq 100$, a5 is a number that satisfies 0 ab 50, and a6 is a number that satisfies $0 \leq a6 \leq 50$, provided that at least one $R^4$ is $R^2$ when a5 is 0.

a4 is $0 \leq a4 \leq 100$, preferably $1 \leq a4 \leq 50$, and further preferably $1 \leq a4 \leq 30$. If a4 is greater than 100, hydrophilicity becomes poor, so that it is difficult to obtain a stable emulsion. a5 is $0 \leq a5 \leq 50$, preferably $1 \leq a5 \leq 30$, and further preferably $1 \leq a5 \leq 10$. If a5 is greater than 50, hydrophilicity becomes too high, so that stability is lost. a6 is $0 \leq a6 \leq 50$, preferably $0 \leq a6 \leq 30$, and further preferably $0 \leq a6 \leq 10$. If a6 is greater than 50, hydrophilicity becomes poor, so that similarly, stability is lost.

The polyether-modified organopolysiloxane (B) has an HLB of 5.0 or less calculated by Griffin's method. An HLB of over 5.0 is not favorable since compatibility to the component (E) becomes degraded.

Such a substance is not limited to the following examples, but for example, "KF-6015", "KF-6017", "KF-6017P", "KF-6028", and "KF-6028P" manufactured by Shin-Etsu Chemical Co., Ltd. can be used.

By using the component (A) and the component (B) in combination, the solubilizing ability to the silicone oil having a kinematic viscosity of 20 mm²/s or less at 25° C., the silicone oil being the component (E) described below, is enhanced, so that the transparency of the appearance is enhanced. If only the component (A) is used, the component (A) is compatible with the component (C), but is not compatible with the component (E). Therefore, by using the component (B) in combination, the component (B) functions as a compatibilizer to the component (E)

In the inventive microemulsion composition, (A)/(B), which is the ratio of the mass of the polyether-modified organopolysiloxane (A) to the mass of the polyether-modified organopolysiloxane (B), is 1.0 to 15.0. Preferably, (A)/(B) is 2.0 to 10.0. Unless (A)/(B) is 1.0 or more, the microemulsion composition does not become stable, and unless (A)/(B) is 15.0 or less, the appearance of the microemulsion composition is degraded.

[Component C]

The glycerol derivative used in the present invention is shown by the following general formula (8).

$$Gly\text{-}\{O\!-\!(PO)_f(EO)_g(BO)_hH\}_3 \tag{8}$$

In the formula, Gly represents a residue in which a hydroxy group is removed from glycerol, PO represents an oxypropylene group, EO represents an oxyethylene group, "f" and "g" are respectively average numbers of moles of PO and EO added, f+g indicates a value of 1 to 30, a mass ratio of PO to EO (PO/EO) is 1/5 to 5/1, BO represents oxyalkylene having 4 carbon atoms, and "h" is an average number of moles of BO added and indicates a value of 1 to 5.

The glycerol derivative is obtained by adding propyleneoxide and ethyleneoxide at a proportion of 3 to 150 molar equivalents based on 1 mol of glycerol, and then adding butylene oxide at a proportion of 3 to 15 molar equivalents based on 1 mol of glycerol. In short, the glycerol derivative is obtained by synthesizing an adduct of PO and EO to glycerol, and then adding butylene oxide in block form.

The mass ratio (PO/EO) of propyleneoxide (PO) to ethyleneoxide (EO) is 1/5 or more in view of enhancing the cleansing effect, and is 5/1 or less in view of enhancing rinsing effect.

The average number of moles of propyleneoxide (PO) and ethyleneoxide (EO) added is 3 to 90 mol in total, that is, f+g is within the range of 1 to 30. If the average number of moles of PO and EO added is less than 3 mol in total, that is, if f+g is less than 1, rinsing property is degraded. If the average number of moles added exceeds 90 mol in total, that is, f+g exceeds 30, the cleansing effect is degraded, and furthermore, spreadability on use is degraded, a sticky feeling of the skin is present, and rinsing property is degraded.

The average number of added moles of alkylene oxide (BO) having 4 carbon atoms is 3 to 15 mol, that is, "h" is within the range of 1 to 5. If the average number of moles of BO added is less than 3 mol, that is, if "h" is less than 1, the cleansing effect is weakened, and a sticky feeling of the skin remains. If the average number of moles added exceeds 15 mol, that is, if "h" exceeds 5, spreadability on use and rinsing property are degraded.

Examples of the alkylene oxide (BO) having 4 carbon atoms include 1,2-butylene oxide, 2,3-butylene oxide, tetramethylene oxide (tetrahydrofuran), etc. In particular, 1,2-butylene oxide is preferable in view of availability, easy reaction control, and so forth.

When these alkylene oxides are added to glycerol, the addition reaction is performed using an alkali catalyst, a phase-transfer catalyst, a Lewis acid catalyst, etc. Generally, an alkali catalyst such as potassium hydroxide is preferably used.

Specific examples of the glycerol derivative (C) include those in which the average number of moles of (EO) added is 8, the average number of moles of (PO) added is 5, and the average number of moles of (BO) added is 3. Polyoxybutylenepolyoxyethylene polyoxypropylene glyceryl ether (3BO) (8EO) (5PO) is preferable in view of reducing shininess on application and reducing superficial feeling. As commercially available products, WILBRIDE 5-753 (manufactured by NOF Corporation) can be used, for example. The present glycerol derivative has an important role of inducing the co-continuous structure described below.

[Component D]

The component (D) used in the present invention is a polyhydric alcohol other than the component (C). Examples of the component D include generally used polyhydric alcohols. Specific examples include sugar alcohols such as erythritol, maltitol, xylitol, and sorbitol; and polyhydric alcohols such as 1,3-BG, glycerol, PG, and DPG. One of these can be used or an appropriate combination of two or more thereof can be used. In particular, a water-soluble glycerol or glycerol derivative other than the component (C) is preferably used.

As the polyhydric alcohol, one of 1,2-alkanediol having 5 to 10 carbon atoms and a polyhydric alcohol other than 1,2-alkanediol having 5 to 10 carbon atoms or a combination of two or more thereof is preferably used. When a polyhydric alcohol is used, HLB can be adjusted by combining with the component (A) polyether-modified organopolysiloxane shown in the general formula (1) having an HLB of 8.0 or more calculated by Griffin's method and the component (B) polyether-modified organopolysiloxane shown in the general formula (7) having an HLB of 5.0 or less calculated by Griffin's method, and a D phase, which is a kind of surfactant phase, can be easily formed.

Specific examples of the 1,2-alkanediol having 5 to 10 carbon atoms include 1,2-pentanediol, 1,2-hexanediol, 1,2-heptanediol, 1,2-octanediol, 1,2-nonanediol, and 1,2-decanediol. In particular, one or more out of 1,2-hexanediol, 1,2-heptanediol, and 1,2-octanediol is preferably used.

The polyhydric alcohol other than 1,2-alkanediol having 5 to 10 carbon atoms is not particularly limited as long as the polyhydric alcohol is used as raw material for cosmetics. Examples thereof include ethylene glycol, diethylene glycol, polyethylene glycol, propylene glycol, dipropylene glycol, polypropylene glycol, glycerol, diglycerol, polyglycerol, 1,3-butyleneglycol, isoprene glycol, sorbitol, mannitol, and glycol.

In this event, the component (D) polyhydric alcohol is preferably glycerol or a glycerol derivative. In particular, dipropylene glycol, glycerol, and 1,3-butyleneglycol are preferable. Furthermore, glycerol is particularly preferable since a D phase can be formed in a wide range of concentrations when glycerol is used.

The total amount of the component (D) polyhydric alcohol blended is preferably 1.0 to 70 mass % of the cosmetic, more preferably 5 to 50 mass %. When the blended amount is 1.0 mass % or more, sufficient microemulsion can be obtained.

[Component E]

The component (E) in the present invention is a silicone oil having a kinematic viscosity of 20 $mm^2$/s or less at 25° C.

The kinematic viscosity is measured by a method described in JIS Z 8809: 2011 by using a Cannon-Fenske viscometer at 25° C.

The silicone oil having the kinematic viscosity of 20 $mm^2$/s or less at 25° C. may be any of linear, branched, or cyclic. Specific examples thereof include dimethyl polysiloxane, methylphenylpolysiloxane, and dimethyl polysiloxane having some methyl groups substituted with alkyl groups having 2 to 20 carbon atoms. The silicone oil may or may not have volatility, but is preferably a volatile oil agent and has a boiling point of 260° C. or lower under one atmospheric pressure.

The volatile silicone oil may be any of linear, branched, or cyclic, and specific examples thereof include linear silicone oil, such as hexamethyldisiloxane, octamethyltrisiloxane, decamethyltetrasiloxane, dodecamethylpentasiloxane, heptamethylethyltrisiloxane, and octamethyldiethyltetrasiloxane; branched silicone oil, such as tris(trimethylsiloxy)methylsilane and tetrakis(trimethylsiloxy)silane; and cyclic silicone oil, such as octamethylcyclotetrasiloxane, decamethylcyclopentasiloxane, dodecamethylcyclohexasiloxane, and tetramethyltetraethylcyclotetrasiloxane. Octamethyltrisiloxane, decamethyltetrasiloxane, dodecamethylpentasiloxane, tris(trimethylsiloxy)methylsilane, tetrakis(trimethylsiloxy) silane, decamethylcyclopentasiloxane, and dodecamethylcyclohexasiloxane are preferable.

In this event, the component (E) is preferably one or more kinds selected from decamethylcyclopentasiloxane, dimethyl polysiloxane, and methylphenylpolysiloxane. These can be used suitably in the inventive microemulsion composition.

[Component F]

The component (F) used in the present invention is water.

[Method for Manufacturing Microemulsion]

A common emulsifying and dispersing apparatus can be used for emulsification, although apparatuses are not particularly limited, and examples thereof include high-speed rotary centrifugal stirrers such as a homogenizing disper, high-speed rotary shear stirrers such as a homomixer, high-pressure jetting emulsifying and dispersing apparatuses such as a homogenizer, a colloid mill, an ultrasonic emulsifier, and the like.

When mixing the six components (A) to (F), a phase inversion temperature emulsification method, a D phase emulsification method, or the like can be employed, for example (emulsification step).

A phase inversion temperature emulsification method is a method of stirring near a phase inversion temperature (PIT) at which the HLB becomes balanced, and then cooling quickly to produce a fine emulsion. Near a PIT, the surface tension between oil and water becomes remarkably low, and therefore, fine emulsified particles are easily produced.

A D phase emulsification method is a method of adding water-soluble polyhydric alcohol to a surfactant to adjust the HLB of the surfactant and form a D phase, then adding oil to go through an O/D emulsion and adding water to produce a fine emulsion.

The microemulsion of the present invention desirably goes through a bicontinuous structure according to the D phase emulsification method. Specifically, the component (E) silicone oil having a kinematic viscosity of 20 $mm^2$/s or less at 25° C. is blended gradually under conditions of shearing with a homogenizing disper into a mixture of a polyether-modified organopolysiloxane (A) having an HLB of 8.0 or more, a polyether-modified organopolysiloxane (B) having an HLB of 5.0 or less, a glycerol derivative (C), and a polyhydric alcohol as the component (D) to form a D phase. A transparent to translucent microemulsion can be obtained by subsequently adding a predetermined amount of water (F) gradually.

There are three types of microemulsions: an aqueous micelle solution phase, where oil is made soluble in water; a reverse micelle oil solution phase, where water is made soluble in oil; and a bicontinuous phase, where both water and oil take on a continuous structure, and a microemulsion falls under one of these phases.

Whether a microemulsion composition is aqueous or oily can be determined by the following method. When several drops of the microemulsion composition are rapidly dispersed homogeneously to excess water after being dropped thereto and are not dispersed to excess oil after being dropped thereto, it is aqueous. On the other hand, when they are rapidly dispersed homogeneously to excess oil after being dropped thereto and are not dispersed to excess water after being dropped thereto, it is oily. An aqueous micelle solution, where oil is made soluble in water, is aqueous since the aqueous micelle solution is rapidly dispersed when added in water, and is not dispersed when added in oil. In the case of a reverse micelle oil solution phase, where water is made soluble in oil, the reverse micelle oil solution phase is oily since it is not dispersed when added in water, and is rapidly dispersed when added in oil. A bicontinuous phase, where both water and oil take on a continuous structure, is either aqueous or oily.

In this event, the inventive microemulsion composition is preferably dispersed when added in water. That is, the inventive microemulsion composition is preferably either an aqueous micelle solution, where oil is made soluble in water, or a bicontinuous phase, where both water and oil take on a continuous structure. Such a microemulsion composition can be used suitably for cosmetics or the like.

Furthermore, whether a microemulsion composition is an aqueous micelle solution phase or a bicontinuous phase can be determined by the following method.

The inventive microemulsion composition preferably forms an aqueous micelle solution phase. It can be confirmed that the composition has an aqueous micelle solution phase by observing an electron microscope image using a freeze-fracture replica technique of known method. More conveniently, it can be confirmed by a solubility test of pigments. In a solubility test of pigments, each of aqueous pigments and oily pigments are added, and if the pigments are rapidly mixed with both water and oil, the obtained microemulsion composition is a bicontinuous phase, and if only the aqueous pigments are dispersed, the composition is an aqueous micelle solution phase.

The inventive microemulsion composition has a transparent to translucent appearance. The average particle size or structural period of the microemulsion is preferably 200 nm or less. At the stage where the water (F) is being added to a white D phase gel containing (A) to (E), the composition goes through a microemulsion having a transparent appearance and having a bicontinuous structure. If the microemulsion has a transparent to translucent appearance when all the water (F) is added, an oil-in-water type microemulsion is obtained.

In the inventive microemulsion composition, 0.1 to 10 wt % of the polyether-modified organopolysiloxane (A) is preferably contained, and further preferably, 1 to 10 wt % is contained. When the polyether-modified organopolysiloxane (A) is within the above ranges, the D phase is easily formed.

In the inventive microemulsion composition, the content ratio of each component (C), (D), (E), and (F) is not particularly limited, but is preferably 0.1 to 10 parts by mass of the component (C) glycerol derivative, 5 to 100 parts by mass of the component (D) polyhydric alcohol, 1 to 50 parts by mass of the component (E) silicone oil, and 10 to 800 parts by mass of the water (F) relative to 10 parts by mass of the component (A) polyether-modified organopolysiloxane having an HLB of 8.0 or more.

[Physical Properties of Microemulsion Composition]

In the inventive microemulsion composition, a silicone-based surfactant is used as an activator and a silicone oil is used as an oil agent, so that anionic or cationic surfactants are not necessarily used. Therefore, the microemulsion composition has characteristics of having little stickiness and little oily feeling originating from activators, being capable of sustaining a light feeling even when blended with make-up. For this reason, by preparing a cleansing material using the microemulsion composition as a base, it is possible to obtain a cleansing agent having excellent spreadability on application, a refreshing feeling, a high cleansing effect, and excellent cleaning performance and stability over time.

[Cosmetics]

The inventive microemulsion composition can be used for various uses, and in particular, is applicable as a raw material of all cosmetics externally used for the skin or hair, and is further applicable for cleansing use. In this case, the blended amount of the microemulsion composition is preferably 0.1 to 40 mass % of the total cosmetic, further preferably 0.1 to 10 mass %. With 0.1 mass % or more, sufficient feeling can be achieved, and with 40 mass % or less, feeling on use and cleansing effect become favorable.

[Other Components]

The inventive microemulsion composition and cosmetics containing the inventive microemulsion composition may be blended with various other components used in usual cosmetics. As other components, an oil agent other than the component (E) as a component (G), a powder as a component (H), a surfactant other than the components (A) and (B) as a component (I), a crosslinked organopolysiloxane as a component (J), a film former as a component (K), and other additives as a component (L) can be contained, for example. One of these can be used or an appropriate combination of two or more thereof can be used. These components are appropriately selected for use depending on the kind of the cosmetic, and so on. The amount of these components to be blended can be a known amount which depends on the kind of the cosmetic, and so on.

Component (G): oil agents other than component (E) One or more oil agents selected from oil agents other than the component (E) can be blended in the inventive cosmetic as the component (G) according to the object. An oil agent in any form of solid, semi-solid, or liquid can be used as long as it is used in usual cosmetics. For example, natural vegetable and animal fats and oils, semi-synthetic fats and oils, hydrocarbon oils, higher alcohols, ester oils, fluorinated oil agents, ultraviolet absorbers, and the like can be used. In a case where an oil agent is blended, the amount of the oil agent blended is not particularly limited, but is preferably 1 to 95 mass %, more preferably 1 to 30 mass % of the total cosmetic. Furthermore, (E)/(G) is preferably 10/0 to 5/5, and is further preferably 10/0 to 8/2. When (E)/(G) is 5/5 or more, the appearance of the microemulsion is favorable.

Natural Vegetable and Animal Fats and Oils and Semi-Synthetic Fats and Oils

Examples of the natural animal and vegetable oils and fats and semi-synthetic oils and fats include avocado oil, linseed oil, almond oil, insects wax, perilla oil, olive oil, cacao butter, kapok wax, kaya oil, carnauba wax, liver oil, candelilla wax, purified candelilla wax, beef tallow, neats foot fat, beef bone fat, hardened beef tallow, apricot kernel oil, whale wax, hardened oil, wheat germ oil, sesame oil, rice germ oil, rice bran oil, sugarcane wax, *Camellia* sasanqua oil, safflower oil, shoa butter, Chinese tung oil, cinnamon oil, jojoba wax, squalano, squalene, shellac wax, turtle oil, soybean oil, tea seed oil, *camellia* oil, evening primrose oil, corn oil, lard, rapeseed oil, Japanese tung oil, bran wax, germ oil, horse fat, persic oil, palm oil, palm kernel oil, castor oil, hardened castor oil, castor oil fatty acid methyl ester, sunflower oil, grape oil, bayberry wax, jojoba oil, macadamia nut oil, bees wax, mink oil, meadowfoam oil, cottonseed oil, cotton wax, Japan wax, Japan wax kernel oil, montan wax, coconut oil, hardened coconut oil, tri-coconut oil fatty acid glyceride, mutton tallow, peanut oil, lanolin, liquid lanolin, reduced lanolin, lanolin alcohol, hard lanolin, lanolin acetate, acetylated lanolin alcohol, lanolin fatty acid isopropyl, POE lanolin alcohol ether, POE lanolin alcohol acetate, lanolin fatty acid polyethylene glycol, POE hydrogenated lanolin alcohol ether, egg yolk oil, etc. Provided that POE means polyoxyethylene.

Hydrocarbon Oils

Examples of the hydrocarbon oils include a linear, branched, and further volatile hydrocarbon oils, etc., and specific examples include ozokerite, α-olefin oligomer, light isoparaffin, isododecane, isohexadecane, light liquid isoparaffin, squalane, synthetic squalane, vegetable squalane, squalene, ceresin, paraffin, paraffin wax, polyethylene wax, polyethylene•polypropylene wax, an (ethylene/propylene/styrene) copolymer, a (butylene/propylene/styrene) copolymer, liquid paraffin, liquid isoparaffin, pristane, polyisobutylene, hydrogenated polyisobutene, microcrystalline wax, vaseline, higher fatty acid, etc. Examples of the higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, etc.

Higher Alcohols

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, POE cholesterol ether, monostearyl glycerol ether (batyl alcohol), monooleyl glyceryl ether (selacyl alcohol), etc.

Ester Oils

Examples of the ester oils include diisobutyl adipate, 2-hexyldecyl adipate, di-2-heptylundecyl adipate, N-alkylglycol morioisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanate, isotridecyl isononanate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, isopropyl lauroyl sarcosinate, diisostearyl malate, and glyceride oil, etc. Examples of the glyceride oil include acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, diglyceryl isostearate/myristate, etc.

Fluorinated Oil Agents

Examples of the fluorinated oil agents include perfluoropolyeLher, perfluorodecalin, perfluorooctane, etc.

Ultraviolet Absorbers

Examples of the ultraviolet absorbers include a benzoic acid-based ultraviolet absorber, such as para-aminobenzoic acid, etc., an anthranilic acid-based ultraviolet absorber, such as methyl anthranilate, etc., a salicylic acid-based ultraviolet absorber, such as methyl salicylate, octyl salicylate, trimethylcyclohexyl salicylate, etc., a cinnamic acid-based ultraviolet absorber, such as octyl para-methoxycinnamate, etc., a benzophenone-based ultraviolet absorber, such as 2,4-dihydroxybenzophenone, etc., an urocanic acid-based ultraviolet absorber, such as ethyl urocanate, etc., a dibenzoylmethane-based ultraviolet absorber, such as 4-t-butyl-4'-methoxy-dibenzoylmethane, etc., phenylbenzimidazole sulfonic acid, a triazine derivative, etc. The ultraviolet absorbers may contain an ultraviolet absorptive scattering agent. Examples of the ultraviolet absorptive scattering agent include powder which absorbs or scatters ultraviolet rays such as fine particulate titanium oxide, fine particulate iron-containing titanium oxide, fine particulate zinc oxide, fine particulate cerium oxide and a complex thereof, etc., and a dispersion in which these powders which absorb and scatter ultraviolet rays are dispersed in the oil agent in advance can also be used.

Component (H): Powder

The powder is not particularly limited as long as it is a raw material that can usually be blended in cosmetics. Examples thereof include pigments, silicone spherical powder, etc. When a powder is blended, the amount of the powder to be blended is not particularly limited, but it is desirable to blend 0.1 to 90 mass %, further preferably 1 to 35 mass % of the entire cosmetic.

The pigments are not particularly limited as long as the pigment is used in normal make-up cosmetics. Examples thereof include inorganic pigments such as talc, mica, sericite, synthetic phlogopite, barium sulfate, aluminum oxide, kaolin, silica, calcium carbonate, zinc oxide, titanium oxide, red iron oxide, yellow iron oxide, black iron oxide, ultramarine blue, Prussian blue, carbon black, titanium suboxide, cobalt violet, chromium oxide, chromium hydroxide, cobalt titanate, bismuth oxychloride, and titanium-mica pearl pigments; organic pigments such as zirconium, barium or aluminum lake such as Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404, and Green No. 3; natural dyes such as chlorophyll and β-carotene; dyes; and the like.

As the above-described powders, those having the particle surface treated can also be used. In addition, the surface treatment agent can preferably provide hydrophobicity with the object of not losing water resistance of the preparation, and is not particularly limited as long as hydrophobicity can be provided. Examples include treatment agents such as silicone treatment agents, waxes, paraffins, organofluorine compounds of perfluoroalkyl and phosphate, etc., surfactants, amino acids such as N-acylglutamic acid, and metallic soaps such as aluminum stearate and magnesium myristate. Silicone treatment agents are more preferable, and examples thereof include silanes or silylation agents such as caprylylsilane (AES-3083 manufactured by Shin-Etsu Chemical Co., Ltd.) or trimethoxysilyl dimethicone, etc., silicone oils such as dimethyl silicone (KF-96A series manufactured by Shin-Etsu Chemical Co., Ltd.), methyl hydrogen polysiloxane (KF-99P, KF-9901, etc. manufactured by Shin-Etsu Chemical Co., Ltd.), silicone-branched silicone treatment agent (KF-9908, KF-9909, etc. manufactured by Shin-Etsu Chemical Co., Ltd.) etc., and acrylic silicone (KP-574 and KP-541 manufactured by Shin-Etsu Chemical Co., Ltd.), etc. Furthermore, one kind of the above-described surface hydrophobizing agent may be used, or two or more kinds thereof may be used in combination. Specific examples of pigments with a surface treatment include the KTP-09 series manufactured by Shin-Etsu Chemical Co., Ltd., in particular, KTP-09W, 09R, 09Y, 09B, etc. Specific examples of dispersions containing hydrophobized fine-particle titanium oxide or hydrophobized fine-particle zinc oxide include SPD-T5, T6, T7, T5L, Z5, Z6, Z5L, etc. manufactured by Shin-Etsu Chemical Co., Ltd. When this component is blended, the component is preferably 0.01 to 95 mass % of the cosmetic.

Examples of the silicone spherical powder include cross-linked silicone powders (i.e., what is called silicone rubber powders of organopolysiloxanes having such a structure that repeating chains of diorganosiloxane units are crosslinked), silicone resin particles (polyorganosilsesquioxane resin particles having a three-dimensional network structure), silicone resin-coated silicone rubber powders, etc. Specific examples of the crosslinked silicone powders and silicone resin particles include those known under names such as (dimethicone/vinyl dimethicone) crosspolymer and polymethylsilsesquioxane, etc. These are commercially available as powder or swollen material containing silicone oil under product names such as, for example, KMP-598, 590, 591, and KSG-016F (all of which are manufactured by Shin-Etsu Chemical Co., Ltd.). These powders provide cosmetics with smoothness by a rolling effect peculiar to spherical powders, and improve feeling on use. One of these can be used or two or more thereof can be used.

Silicone resin-coated silicone rubber powders are particularly favorable since silicone resin-coated silicone rubber powders have the effect of improving feeling, for example, preventing stickiness, etc. and the effect of correcting unevenness of wrinkles and pores, etc. and the like. Specific examples of the silicone resin-coated silicone rubber powders are known under names of (vinyl dimethicone/methicone silsesquioxane) crosspolymer, (diphenyl dimethicone/vinyldiphenyl dimethicone/silsesquioxane) crosspolymer, polysilicone-22, and polysilicone-1 crosspolymers, etc., which are defined in Cosmetic-Info.jp. These are commercially available under product names such as KSP-100, 101, 102, 105, 300, 411, and 441 (all of which are manufactured by Shin-Etsu Chemical Co., Ltd.). One of these powders can be used or two or more thereof can be used. When this component is blended, the component is preferably 0.01 to 95 mass % of the cosmetic.

Component (I): Surfactant Other than Components (A) and (B)

The surfactant other than the components (A) and (B) includes nonionic, anionic, cationic, and amphoteric surfactants that do not contain a silicone skeleton, a polyether-modified organopolysiloxane having an HLB of 5.0 to 8.0 calculated by Griffin's method, polyglycerol-modified silicone, crosslinked polyether-modified silicone, and crosslinked polyglycerol-modified silicone, but is not particularly limited, and any of these can be used as long as it is used in usual cosmetics. One of these can be used or an appropriate combination of two or more thereof can be used. Among these surfactants, surfactants containing a silicone skeleton are preferable in view of compatibility with the components (A) and (B).

In these surfactants, the content of hydrophilic polyoxy-ethylene groups, polyoxyethylene-polyoxypropylene groups, or polyglycerol residues is preferably 10 to 70% in the molecule. Specific examples of such surfactants include KSG-210, 240, 310, 320, 330, 340, 320Z, 350Z, 710, 810, 820, 830, 840, 820Z, 850Z, KF-6012, 6100, 6104, 6105, and 6106, manufactured by Shin-Etsu Chemical Co., Ltd., and the like.

When the component (I) is blended, the blended amount is preferably 0.01 to 15 mass % in the cosmetic.

Component (J): Crosslinked Organopolysiloxane

The crosslinked organopolysiloxane is not particularly limited as long as it is used in usual cosmetic products. One of the crosslinked organopolysiloxane can be used or an appropriate combination of two or more thereof can be used.

Unlike the silicone spherical powders described in the component (H) above, the crosslinked organopolysiloxane does not have a spherical shape.

In addition, unlike the component (I) surfactant other than the components (A) and (B), the component (J) is preferably a compound having no polyether- or polyglycerol structure in the molecular structure, and is preferably an elastomer having structural viscosity by swelling with the oil agent. Specific examples of the crosslinked organopolysiloxane include (dimethicone/vinyl dimethicone) crosspolymers, (dimethicone/phenylvinyl dimethicone) crosspolymers, (vinyl dimethicone/lauryl dimethicone) crosspolymers, (lauryl polydimethylsiloxyethyl dimethicone/bis-vinyl dimethicone) crosspolymers, and the like, which are defined in Cosmetic-Info.jp. These are commercially available as swollen materials containing oil which is liquid at room temperature. Specific examples thereof include KSG-15, 1510, 16, 1610, 18A, 19, 41A, 42A, 43, 44, 042Z, 045Z, and 048Z, which are manufactured by Shin-Etsu Chemical Co., Ltd., and the like.

When the component (J) is blended, the blended amount is preferably 0.01 to 30 mass % in the cosmetic as solid contents.

Component (K): Film Former

As the film former, existing film formers can be used in combination. The existing film formers are not particularly limited as long as the raw material can be blended in usual cosmetics. Specifically, used as the film former are: latexes such as polyvinyl alcohol, polyvinylpyrrolidone, polyvinyl acetate, and polyalkyl acrylate; cellulose derivatives such as dextrin, alkyl cellulose and nitrocellulose; siliconized poly-saccharides such as pullulan tri(trimethylsiloxy)silylpropy-lcarbamate; acrylic-silicone graft copolymers such as (alkyl acrylate/dimethicone) copolymers; silicone resins such as trimethylsiloxysilicate; silicone-based resins such as sili-cone-modified polynorbornene and fluorine-modified sili-cone resins; fluorinated resins, aromatic hydrocarbon resins, polymer emulsion resins, terpene-based resins, polybutene, polyisoprene, alkyd resins, polyvinylpyrrolidone-modified polymers, rosin-modified resins, polyurethanes, and the like.

Among these, silicone-based film formers are particularly preferable. Above all, it is possible to use pullulan tri (trimethylsiloxy)silylpropyl carbamate (commercially available products, dissolved in a solvent, include TSPL-30-D5 and ID manufactured by Shin-Etsu Chemical Co., Ltd.), (alkyl acrylate/dimethicone) copolymers (commercially available products, dissolved in a solvent, include KP-543, 545, 549, 550, and 545L manufactured by Shin-Etsu Chemical Co., Ltd., and the like), trimethylsiloxysilicate (commercially available products, dissolved in a solvent, include KF-7312J and X-21-5250 manufactured by Shin-Etsu Chemical Co., Ltd., and the like), silicone-modified polynor-bornene (commercially available products, dissolved in a solvent, include NBN-30-ID manufactured by Shin-Etsu Chemical Co., Ltd., and the like), an organosiloxane graft polyvinyl alcohol polymer, and the like. However, the film former is not limited thereto.

When the component (K) is blended, the blended amount is preferably 0.1 to 20 mass % in the cosmetic.

Component (L): Other Additives

Examples of the other additives include an oil-soluble gelling agent, water-soluble thickening agent, antiperspirant, preservative and antimicrobial, perfume, salt, antioxidant, pH adjuster, chelator, refrigerant, anti-inflammatory agent, skincare component (such as whitening agent, cell activator, rough skin improver, blood circulation promoter, skin astringent, antiseborrheic agent), vitamin, amino acid, nucleic acid, hormone, inclusion compound, and the like. One of these components (L) can be used or an appropriate combination of two or more thereof can be used. When the component (L) is blended, the blended amount is preferably 0.1 to 20 mass % in the cosmetic.

Oil-Soluble Gelling Agent

The oil-soluble gelling agent includes metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitic acid ester, dextrin stearic acid ester, and dextrin 2-ethylhexanoic acid/palmitic acid ester; sucrose fatty acid esters such as sucrose palmitic acid ester and sucrose stearic acid ester; fructo-oligosaccharide fatty acid esters such as fructo-oligosaccharide stearic acid ester and fructo-oligosaccharide 2-ethylhexanoic acid ester; benzylidene derivatives of sorbitol such as monobenzylidene sorbitol and dibenzylidene sorbitol; organic-modified clay minerals of disteardimonium hectorite, stearalkonium hectorite, and hectorite; and the like.

Water-Soluble Thickening Agent

Examples of the water-soluble thickening agent include plant polymers such as an Arabia gum, tragacanth, galactan, a carob gum, a guar gum, a karaya gum, carrageenan, pectin, agar, quince seed (marmelo), starch (rice, corn, potato, wheat, and so on), an algae colloid, a trant gum, a locust bean gum; microbial polymers such as a xanthan gum, dextran, succinoglucan, and pullulan; animal polymers such as collagen, casein, albumin, and gelatin; starch polymers such as carboxymethyl starch and methyl hydroxypropyl starch; cellulose polymers such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, cationized cellulose, and cellulose powder; alginic acid polymers such as sodium alginate and propylene glycol alginate ester; vinyl polymers such as polyvinyl methyl ether and carboxy vinyl polymer; a polyoxyethylene polymer; polyoxyethylene polyoxypropylene copolymer polymers; acryl polymers such as sodium polyacrylate, polyethyl acrylate, polyacrylamide, and an acryloyldimethyl taurate salt copolymer; other synthetic water-soluble polymers such as polyethyleneimine and a cationic polymer; inorganic water-soluble polymers such as a bentonite, aluminum magnesium silicate, montmorillonite, beidellite, nontronite, saponite, hectorite, anhydrous silicic acid; and the like.

Among them, one or a combination of two or more water-soluble thickening agents selected from plant polymers, microbial polymers, animal polymers, starch polymers, cellulose polymers, alginic acid polymers, polyoxyethylene polyoxypropylene copolymer polymers, acryl polymers, and inorganic water-soluble polymers are preferably used.

Antiperspirant

Examples of the antiperspirant include aluminum hydroxyhalides such as chlorohydroxy aluminum and aluminum chlorohydroxy allantoinate; aluminum halides such as aluminum chloride; aluminum allantoinate, tannic acid, persimmon tannin, potassium aluminum sulfate, zinc oxide, zinc para-phenolsulfonate, burnt alum, aluminum zirconium tetrachlorohydrate, aluminum zirconium trichlorohydrex glycine, and the like. In particular, as components that exhibit a high effect, aluminum hydroxyhalide, aluminum halide, and a complex or mixture thereof with zirconyl oxyhalide and zirconyl hydroxyhalide (for example, aluminum zirconium tetrachlorohydrate and aluminum zirconium trichlorohydrex glycine), and the like are preferable.

Preservative and Antimicrobial

The preservative and antimicrobial include para-oxybenzoate alkyl ester, benzoic acid, sodium benzoate, sorbic acid, potassium sorbate, phenoxy ethanol, imidazolidinyl urea, salicylic acid, isopropylmethylphenol, carbolic acid, p-chloro-m-cresol, hexachlorophene, benzalkonium chloride, chlorhexidine chloride, trichlorocarbanilide, iodopropynyl butylcarbamate, polylysine, photosensitizers, silver, plant extracts, and the like.

Perfume

Examples of the perfume include natural perfumes and synthetic perfumes. Examples of the natural perfume include vegetable perfume separated from flowers, leaves, wood, pericarp, etc.; and animal perfume such as musk, civet, etc. Examples of the synthetic perfume include hydrocarbons such as monoterpene, etc.; alcohols such as an aliphatic alcohol, an aromatic alcohol, etc.; aldehydes such as terpene aldehyde, aromatic aldehyde, etc.; ketones such as an alicyclic ketone, etc.; esters such as a terpene-based ester, etc.; lactones; phenols; oxides; nitrogen-containing compounds; acetals, etc.

Salt

Examples of the salt include an inorganic salt, an organic acid salt, an amine salt and an amino acid salt. Examples of the inorganic salt include a sodium salt, a potassium salt, a magnesium salt, a calcium salt, an aluminum salt, a zirconium salt, a zinc salt, etc., of an inorganic acid such as hydrochloric acid, sulfuric acid, carbonic acid, nitric acid, etc. Examples of the organic acid salt include salts of an organic acid such as acetic acid, dehydroacetic acid, citric acid, malic acid, succinic acid, ascorbic acid, stearic acid, etc. Examples of the amine salt and the amino acid salt include a salt of an amine such as triethanolamine, etc., and a salt of an amino acid such as glutamic acid, etc. In addition, as others, a salt of hyaluronic acid, chondroitin sulfuric acid, etc., and further an acid-alkali neutralizing salt used in preparation prescription can be also used.

Antioxidant

Examples of the antioxidant are not particularly limited, and include carotenoid, ascorbic acid and a salt thereof, ascorbyl stearate, ocopherol acetate, tocopherol, p-t-butylphenol, butylhydroxyanisol, dibutylhydroxytoluene, phytic acid, ferulic acid, thiotaurine, hypotaurine, sulfite, erythorbic acid and a salt thereof, chlorogenic acid, epicatechin, epigallocatechin, epigallocatechin gallate, apigenin, campherol, myricetin, quercetin, and the like.

pH Adjuster

Examples of the pH adjuster include lactic acid, citric acid, glycolic acid, succinic acid, tartaric acid, dl-malic acid, potassium carbonate, sodium bicarbonate, ammonium bicarbonate, and the like.

Chelator

Examples of the chelator include alanine, sodium edetate, sodium polyphosphate, sodium metaphosphate, phosphoric acid, and the like.

Refrigerant

Examples of the refrigerant include L-menthol, camphor, menthyl lactate, and the like.

Anti-Inflammatory Agent

Examples of the anti-inflammatory agent include allantoin, glycyrrhizinic acid and a salt thereof, glycyrrhetinic acid and stearyl glycyrrhetinate, tranexamic acid, azulene, and the like.

Skincare Component

Examples of the skincare component include a skin-brightening agent such as a placenta extract, arbutin, glutathione, and strawberry geranium extract; a cell activator such as royal jelly, a photosensitizer, a cholesterol derivative, and a calf blood extract; a rough skin-improving agent, a blood circulation promoter such as vanillylamide nonylate, benzyl nicotinate, β-butoxyethyl nicotinate, capsaicin, zingerone, cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthine, and γ-orizanol; a skin astringent, an antiseborrheic agent such as sulfur and thianthrol, and the like.

Vitamin

Examples of the vitamin include vitamin A such as vitamin A oil, retinol, retinol acetate, and retinol palmitate; vitamin B including vitamin $B_2$ such as riboflavin, riboflavin butyrate, and flavin adenine nucleotide, vitamin $B_6$ such as pyridoxine hydrochloride, pyridoxine dioctanoate, and pyridoxine tripalmitate, vitamin $B_{12}$ and a derivative thereof, and vitamin Bis and a derivative thereof; vitamin C such as L-ascorbic acid, L-ascorbic acid dipalmitate, sodium L-ascorbic acid-2-sulfate, and dipotassium L-ascorbic acid diphosphate; vitamin D such as ergocalciferol and cholecalciferol; vitamin E such as α-tocopherol, β-tocopherol, γ-tocopherol, dl-α-tocopherol acetate, dl-α-tocopherol nicotinate, and dl-α-tocopherol succinate; nicotinic acids such as nicotinic acid, benzyl nicotinate, and amide nicotinate; pantothenic acids such as vitamin H, vitamin P, calcium pantothenate, D-pantothenyl alcohol, pantothenyl ethyl other, and acetyl pantothenyl ethyl ether; biotin, and the like.

Amino Acid

Examples of the amino acid include glycine, valine, leucine, isoleucine, serine, threonine, phenylalanine, arginine, lysine, aspartic acid, glutamic acid, cystine, cysteine, methionine, tryptophan, and the like.

Nucleic Acid

Examples of the nucleic acid include deoxyribonucleic acid, and the like.

Hormone

Examples of the hormone include estradiol, ethenyl estradiol, and the like.

Inclusion Compound

Examples of the inclusion compound include cyclodextrin, and the like.

The cosmetic in the present invention is not particularly limited, and is preferably applied to cleansing agents, skincare cosmetics, hair cosmetics, make-up cosmetics, sun protection cosmetics, etc.

The physical form of the inventive cosmetic can be selected from various physical forms such as liquid, cream, solid, paste, gel, mousse, souffle, clay, powder, and stick forms.

EXAMPLE

Hereinafter, the present invention will be described more specifically with reference to Examples.

However, the present invention is not limited to the following Examples.

Examples 1 to 12, Comparative Examples 1 to 10

Emulsions were prepared according to the compositions shown in Tables 1 and 2. The blended amounts are shown by mass %.

[Component (A)]

KF-6013 (HLB=10.0, Shin-Etsu Chemical Co., Ltd.) as a polyether-modified organopolysiloxane (A) having an HLB of 8.0 or more calculated by Griffin's method.

[Component (B)]

KF-6017 (HLB=4.5, Shin-Etsu Chemical Co., Ltd.) and KF-6028 (HLB=3.5, Shin-Etsu Chemical Co., Ltd.) as polyether-modified organopolysiloxanes (B) having an HLB of 5.0 or less calculated by Griffin's method.

[Component (C)]

WILBRIDE S-753 (NOF Corporation) as a glycerol derivative (C).

[Component (D)]

As a component (D), glycerol and ethylhexyl glycerol were charged into a 200-mL glass beaker as polyhydric alcohols other than the component (C), and the mixture was stirred and dissolved at room temperature using a disper.

[Component (E)]

After stirring and dissolving the component (D), decamethylcyclopentasiloxane (KF-995), being a cyclic organopolysiloxane having a kinematic viscosity of 4 $mm^2$/s, KF-96A-6cs, being a linear dimethyl polysiloxane having a kinematic viscosity of 6 $mm^2$/s, and KF-56A, being a phenyl-modified organopolysiloxane (all Shin-Etsu Chemical Co., Ltd.) as component (E) silicone oils having a kinematic viscosity of 20 $mm^2$/s or less at 25° C.

A D phase was formed by blending the components (A) to (E) gradually under room temperature.

[Component (F)]

After that, an emulsion was prepared by adding a predetermined amount of water (F) gradually under room temperature. The blended amount is shown by mass %.

[Component (G)]

In Examples 8 to 12, squalane, isododecane, and 2-ethylhexyl palmitate were blended according to the compositions shown in Table 1.

Water dispersibility was investigated by adding one drop of the emulsion prepared in Examples 1 to 12 and Comparative Examples 1 to 10 to 10 ml of water (water dispersibility test). Similarly, oil dispersibility was investigated by adding one drop of the microemulsion to 10 ml of a decamethylcyclopentasiloxane solution (oil dispersibility test). Tables 1 and 2 show the results along with the evaluation of the appearance of the emulsion at 25° C.

A pigment solubility test was conducted on microemulsions (Examples 1 to 12) obtained in a colorless and transparent or translucent state. As test methods, the water solubility was investigated by adding an aqueous water-soluble pigment (Blue #1) solution (concentration: 0.1 mass %) to the obtained microemulsion. Meanwhile, the oil solubility was investigated in the same manner as above by adding a solution of an oil-soluble pigment (β-carotene) in decamethylcyclopentasiloxane (concentration: 1.0 mass %) to the obtained microemulsion. Table 1 shows the results along with the evaluation of the appearance of the microemulsion at 25° C.

| | | | Example 1 | Example 2 | Example 3 | Example 4 | Example 5 | Example 6 |
|---|---|---|---|---|---|---|---|---|
| Formulated composition (mass %) | (A) | KF-6013 (HLB = 10.0) | 4.5 | 4.5 | 4.0 | 3.5 | 4.5 | 4.5 |
| | (B) | KF-6017 (HLB = 4.5) | 1.1 | | | | | |
| | | KF-6028 (HLB = 3.5) | | 1.1 | 1.6 | 2.1 | 1.1 | 1.1 |
| | (C) | Polyoxybutylene-polyoxyethylene polyoxypropylene glyceryl ether (3BO) (8EO) (5PO) (WILBRIDE S-753, manufactured by NOF Corporation) | 0.5 | 0.5 | 0.5 | 0.5 | 0.9 | 0.5 |
| | (D) | Glycerol | 26.6 | 26.6 | 26.6 | 26.6 | 26.6 | 26.6 |
| | | Ethylhexyl glycerol | 0.4 | 0.4 | 0.4 | 0.4 | | 0.4 |
| | (E) | KF-995 | | | | | | 2.0 |
| | | KF-96A-6cs | 2.0 | 2.0 | 2.0 | 2.0 | 2.0 | |
| | | KF-5 6A | | | | | | |
| | (F) | Water | 64.9 | 64.9 | 64.9 | 64.9 | 64.9 | 64.9 |
| | (G) | Squalane | | | | | | |
| | | Isododecane | | | | | | |
| | | 2-ethylhexyl palmitate | | | | | | |
| | | (A)/(B) | 4.1 | 4.1 | 2.5 | 1.7 | 4.1 | 4.1 |
| | | Total | 100 | 100 | 100 | 100 | 100 | 100 |
| | | Appearance of emulsion | Transparent | Transparent | Transparent | Translucent | Transparent | Transparent |
| Pigment solubility test | | Water solubility | Good | Good | Good | Good | Good | Good |
| | | Oil solubility | Poor | Poor | Poor | Poor | Poor | Poor |
| | | Water dispersibility test | Good | Good | Good | Good | Good | Good |
| | | Oil dispersibility test | Poor | Poor | Poor | Poor | Poor | Poor |

| | | | Example 7 | Example 8 | Example 9 | Example 10 | Example 11 | Example 12 |
|---|---|---|---|---|---|---|---|---|
| Formulated composition (mass %) | (A) | KF-6013 (HLB = 10.0) | 4.5 | 4.5 | 4.0 | 4.5 | 4.5 | 4.5 |
| | (B) | KF-6017 (HLB = 4.5) | | | 1.1 | | | |
| | | KF-6028 (HLB = 3.5) | 1.1 | 1.1 | | 1.1 | 1.1 | 1.1 |
| | (C) | Polyoxybutylene-polyoxyethylene polyoxypropylene glyceryl ether (3BO) (8EO) (5PO) (WILBRIDE S-753, manufactured by NOF Corporation) | 0.5 | 0.5 | 1.0 | 0.5 | 0.5 | 0.5 |
| | (D) | Glycerol | 26.6 | 26.6 | 26.6 | 26.6 | 26.6 | 26.6 |
| | | Ethylhexyl glycerol | 0 4 | 0.4 | 0.4 | 0.4 | 0.4 | 0.4 |
| | (E) | KF-995 | | | | | | |
| | | KF-96A-6cs | | 1.0 | 1.5 | 1.5 | 1.5 | |
| | | KF-5 6A | 2.0 | | | | | 1.5 |
| | (F) | Water | 64.9 | 64.9 | 64.9 | 64.9 | 64.9 | 64.9 |
| | (G) | Squalane | | 1.0 | 0.5 | | | 0.5 |
| | | Isododecane | | | | 0.5 | | |
| | | 2-ethylhexyl palmitate | | | | | 0.5 | |
| | | (A)/(B) | 4.1 | 4.1 | 3.6 | 4.1 | 4.1 | 4.1 |
| | | Total | 100 | 100 | 100 | 100 | 100 | 100 |
| | | Appearance of emulsion | Transparent | Translucent | Translucent | Translucent | Translucent | Translucent |
| Pigment solubility test | | Water solubility | Good | Good | Good | Good | Good | Good |
| | | Oil solubility | Poor | Poor | Poor | Poor | Poor | Poor |
| | | Water dispersibility test | Good | Good | Good | Good | Good | Good |
| | | Oil dispersibility test | Poor | Poor | Poor | Poor | Poor | Poor |

TABLE 2

|  |  |  | Comparative Example 1 | Comparative Example 2 | Comparative Example 3 | Comparative Example 4 | Comparative Example 5 | Comparative Example 6 |
|---|---|---|---|---|---|---|---|---|
| Formulated composition (mass %) | (A) | KF-6013 (HLB = 10.0) | 5.6 | 4.5 | 4.5 |  | 4.5 | 4.5 |
|  | (B) | KF-6017 (HLB = 4.5) |  | 1.1 |  | 5.6 | 1.1 | 1.1 |
|  |  | KF-6028 (HLB = 3.5) |  |  | 1.1 |  |  |  |
|  | (C) | Polyoxybutylene-polyoxyethylene polyoxypropylene glyceryl ether (3BO) (8EO) (5PO) (WILBRIDE S-753, manufactured by NOF Corporation) | 0.5 |  |  | 0.5 | 0.5 | 0.5 |
|  | (D) | Glycerol | 26.6 | 26.6 | 26.6 | 26.6 | 26.6 | 26.6 |
|  |  | Ethylhexyl glycerol | 0.4 | 0.9 | 0.9 | 0.4 | 0.4 | 0.4 |
|  | (E) | KF-995 |  |  |  |  |  |  |
|  |  | KF-96A-6cs | 2.0 | 2.0 | 2.0 | 2.0 |  |  |
|  |  | KF-56A |  |  |  |  |  |  |
|  | (F) | Water | 64.9 | 64.9 | 64.9 | 64.9 | 64.9 | 64.9 |
|  | (G) | Squalane |  |  |  |  | 2.0 |  |
|  |  | Isododecane |  |  |  |  |  | 2.0 |
|  |  | 2-ethylhexyl palmitate |  |  |  |  |  |  |
|  |  | (A)/(B) | — | 4.1 | 4.1 | — | 4.1 | 4.1 |
|  |  | Total | 100 | 100 | 100 | 100 | 100 | 100 |
|  |  | Appearance of emulsion | Clouded | Clouded | Clouded | Separated | Separated | Separated |
|  |  | Water dispersibility test | Good | Good | Good | — | — | — |
|  |  | Oil dispersibility test | Poor | Poor | Poor | — | — | — |

|  |  |  | Comparative Example 7 | Comparative Example 8 | Comparative Example 9 | Comparative Example 10 |
|---|---|---|---|---|---|---|
| Formulated composition (mass %) | (A) | KF-6013 (HLB = 10.0) | 4.5 | 2.5 | 1.5 | 5.3 |
|  | (B) | KF-6017 (HLB = 4.5) | 1.1 | 3.1 | 4.1 | 0.3 |
|  |  | KF-6028 (HLB = 3.5) |  |  |  |  |
|  | (C) | Polyoxybutylene-polyoxyethylene polyoxypropylene glyceryl ether (3BO) (8EO) (5PO) (WILBRIDE S-753, manufactured by NOF Corporation) | 0.5 | 0.5 | 0.5 | 0.5 |
|  | (D) | Glycerol | 26.6 | 26.6 | 26.6 | 26.6 |
|  |  | Ethylhexyl glycerol | 0.4 | 0.4 | 0.4 | 0.4 |
|  | (E) | KF-995 |  |  |  |  |
|  |  | KF-96A-6cs |  | 2.0 | 2.0 | 2.0 |
|  |  | KF-56A |  |  |  |  |
|  | (F) | Water | 64.9 | 64.9 | 64.9 | 64.9 |
|  | (G) | Squalane |  |  |  |  |
|  |  | Isododecane |  |  |  |  |
|  |  | 2-ethylhexyl palmitate | 2.0 |  |  |  |
|  |  | (A)/(B) | 4.1 | 0.8 | 0.4 | 17.7 |
|  |  | Total | 100 | 100 | 100 | 100 |
|  |  | Appearance of emulsion | Separated | Separated | Separated | Clouded |
|  |  | Water dispersibility test | — | — | — | Good |
|  |  | Oil dispersibility test | — | — | — | Poor |

As in the above Table 1, microemulsions having a transparent to translucent appearance were obtained in Examples 1 to 12. When the microemulsions were dropped into water, each microemulsion dispersed homogenously, and thus, dispersibility in water was confirmed.

A pigment solubility test was conducted on the microemulsions obtained in Table 1. Only the water-soluble pigment was dissolved, and thus, it was confirmed that the microemulsions had a water-soluble micelle structure (oil-in-water type microemulsion).

As in the above Table 2, emulsions having a clouded appearance or emulsions in a separated state were obtained in Comparative Examples 1 to 10. When the clouded emulsions were dropped into water, each emulsion dispersed homogeneously, and thus, dispersibility in water was confirmed. In Comparative Example 1, emulsification was performed using only (A) without using the compatibilizer (B) in combination, and therefore, compatibility with (E) was low, so that the appearance was clouded. In Comparative Examples 2 and 3, (C), which is a D-phase inducing agent, was not contained, so that the emulsion did not go through a D phase and became clouded. In Comparative Example 4, (A), which is an activator, was not contained, so that emulsification was difficult, and the emulsion was separated. In Comparative Examples 5 to 7, (G) was used alone without using (E), which has high compatibility with (A) and (B), so that compatibility was not achieved, and the emulsion was separated. In Comparative Examples 8 to 10, the mass ratio (A)/(B) was outside the range of 1.0 to 15.0, so that the emulsions had a separated or clouded appearance.

Using the Examples 1, 4, 6, 7, and 10, and Comparative Examples 1 and 3 prepared in Table 1, performance evaluation ("feeling on application", "cleansing effect", "feeling after cleaning", and "storage stability") of the cleansing materials was carried out. The results are shown in Table 3.

[Feeling on Application]

Ten expert panelists applied 2 g of the cleansing material prepared above to the left arm, and a distance of 3 cm was massaged with the forefinger of the right hand at a rate of 6 cm/second for 1 minute. The spreadability after 1 minute was evaluated by the following criteria (5 to 1), and has been shown by the total number of points of the ten panelists.

<Evaluation Criteria>
5: when spreadability on the skin felt very good
4: when spreadability on the skin felt good
3: when spreadability on the skin felt rather good
2: when spreadability on the skin felt rather poor
1: when spreadability on the skin felt poor <Five-Rank Evaluation According to Total of Marks>
S: when the total of marks was 40 to 50
A: when the total of marks was 30 to less than 40
B: when the total of marks was 20 to less than 30
C: when the total of marks was 10 to less than 20
D: when the total of marks was less than 10

[Cleansing Effect]

Ten expert panelists applied 2 g of the cleansing material prepared above on the left arm, which had been made-up, and a distance of 3 cm was massaged with the forefinger of the right hand at a rate of 6 cm/second for 1 minute. After that, the arm was washed with water for 10 seconds. Then, the cleansing effect was evaluated by the following criteria (5 to 1), and has been shown by the total number of points of the ten panelists.

<Evaluation Criteria>
5: when the make-up came off extremely well, and a sufficient cleansing effect was actually felt
4: when the make-up came off well, and a cleansing effect was actually felt 3: when the make-up came off rather well, and a cleansing effect was rather felt
2: when the make-up came off rather poorly, and a cleansing effect was not very well felt
1: when the make-up came off poorly, and a cleansing effect was not actually felt <Five-Rank Evaluation According to Total of Marks>
S: when the total of marks was 40 to 50
A: when the total of marks was 30 to less than 40
B: when the total of marks was 20 to less than 30
C: when the total of marks was 10 to less than 20
D: when the total of marks was less than 10

[Feeling After Cleaning]

Ten expert panelists applied 2 g of the cleansing material prepared above on the left arm, which had been made-up, and a distance of 3 cm was massaged with the forefinger of the right hand at a rate of 6 cm/second for 1 minute. After that, the arm was washed with water for 10 seconds. Then, feelings including the remaining feeling on the skin was evaluated by the following criteria (5 to 1), and has been shown by the total number of points of the ten panelists.

<Evaluation Criteria>
5: when there was clearly no remaining feeling, and a sufficient refreshing feeling was felt
4: when there was no remaining feeling, and a refreshing feeling was felt
3: when there was not much remaining feeling, and a rather refreshing feeling was felt
2: when there was some remaining feeling, and a refreshing feeling was not much felt
1: when there was a remaining feeling, and a refreshing feeling was not felt <Five-Rank Evaluation According to Total of Marks>
S: when the total of marks was 40 to 50
A: when the total of marks was 30 to less than 40
B: when the total of marks was 20 to less than 30
C: when the total of marks was 10 to less than 20
D: when the total of marks was less than 10

[Storage Stability]

10 g of each cleansing material was loaded into a glass bottle and sealed, and then were stored in a thermostat at 50 degrees and 5 degrees for 1 month. The appearance of the samples after storage was observed, and storage stability was evaluated by the following criteria.

<Evaluation Criteria>
Good: when no change was observed in appearance under either of the temperature conditions
Poor: when a change was observed in appearance under either of the temperature conditions

TABLE 3

|  | Example 1 | Example 4 | Example 6 | Example 7 | Example 10 | Comparative Example 1 | Comparative Example 3 |
|---|---|---|---|---|---|---|---|
| Feeling on application | S | S | S | A | A | C | D |
| Cleansing effect | S | A | S | S | S | B | C |
| Feeling after cleaning | A | A | S | A | A | C | D |
| Storage stability | Good | Good | Good | Good | Good | Good | Poor |

Sufficient performance was not achieved in Comparative Examples 1 and 3. In Comparative Examples 1 and 3, the appearance was clouded, and oil-in-water type emulsions having a large particle size were obtained. Accordingly, spreadability on the skin, cleansing effect, and feeling after cleaning were insufficient. Particularly, in Comparative Example 3, the component (C) was not contained, so that storage stability was low, and the emulsion was separated.

On the other hand, it can be observed that the microemulsion compositions of the Examples 1, 4, 6, 7, and 10 of the present invention are all usable as a cleansing agent having favorable spreadability on application, a refreshing feeling, a high cleansing effect, excellent cleaning performance, and favorable storage stability.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A microemulsion composition comprising:

(A) a polyether-modified organopolysiloxane shown in the following general formula (1) having an HLB of 8.0 or more calculated by Griffin's method,

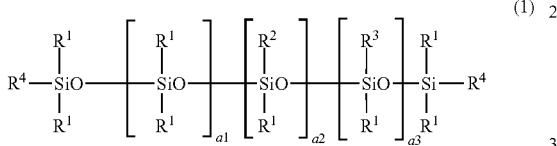

(1)

wherein $R^1$s represent identical or different types of alkyl groups, aryl groups, or aralkyl groups having 1 to 30 carbon atoms or halogen-substituted groups, amino-substituted groups, or carboxy-substituted groups thereof, $R^2$s represent identical or different polyoxyalkylene groups shown by the following general formula (2), $$(CH_2)_2\text{-}C_lH_{2l}\text{—}O\text{—}(C_2H_{40})_b(C_3H_6O)_cR^5 \qquad (2)$$

wherein $R^5$ represents an unsubstituted or substituted monovalent hydrocarbon group or a hydrogen atom, "l", "b", and "c" are integers that satisfy $0 \leq l \leq 15$, $2 \leq b \leq 200$, $0 \leq c \leq 200$, and $3 \leq b+c \leq 200$, $R^3$s represent identical or different types of groups shown by one of the following general formulae (3) to (6), $$—(CH_2)_2—C_mH_{2m}—(SiOR^1{}_2)_d—SiR^1{}_3 \qquad (3)$$

$$—(CH_2)_2—C_mH_{2m}—SiR^1{}_{e1}—(OSiR^1{}_3)_{3-e1} \qquad (4)$$

$$—(CH_2)_2—C_mH_{2m}—SiR^1{}_{e1}—(OSiR^1{}_{e2} \\ (OSiR^1{}_3)_{3-e2})_{3-e1} \qquad (5)$$

$$—(CH_2)_2—C_mH_{2m}—SiR^1{}_{e1}—(OSiR^1{}_{e2}(OSiR^1{}_{e3} \\ (OSiR^1{}_3)_{3-e3})_{3-e2})_{3-e1} \qquad (6)$$

wherein $R^1$ is as described above and "m", "d", and e1 to e3 are integers that satisfy $0 \leq m \leq 5$, $0 \leq d \leq 500$, $0 \leq e1 \leq 2$, $0 \leq e2 \leq 2$, and $0 \leq e3 \leq 2$, $R^4$s are each independently $R^1$, $R^2$, or $R^3$, a1 is a number that satisfies $0 \leq a1 \leq 100$, a2 is a number that satisfies $0 \leq a2 \leq 50$, and a3 is a number that satisfies $0 \leq a3 \leq 50$, provided that at least one $R^4$ is $R^2$ when a2 is 0;

(B) a polyether-modified organopolysiloxane shown in the following general formula (7) having an HLB of 5.0 or less calculated by Griffin's method,

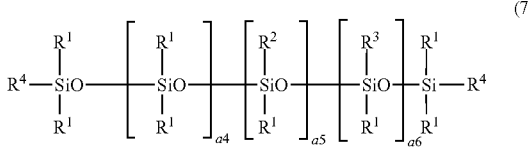

(7)

wherein $R^1$, $R^2$, $R^3$, and $R^4$ follow the above definitions, a4 is a number that satisfies $0 \leq a4 \leq 100$, a5 is a number that satisfies $0 \leq a5 \leq 50$, and a6 is a number that satisfies $0 \leq a6 \leq 50$, provided that at least one $R^4$ is $R^2$ when a5 is 0;

(C) a glycerol derivative shown in the following general formula (8), $$Gly\text{-}\{O\text{—}(PO)_f(EO)_g(BO)_hH\}_3 \qquad (8)$$

wherein Gly represents a residue in which a hydroxy group is removed from glycerol, PO represents an oxypropylene group, EO represents an oxyethylene group, "f" and "g" are respectively average numbers of moles of PO and EO added, f+g indicates a value of 1 to 30, a mass ratio of PO to EO, that is, PO/EO is 1/5 to 5/1, BO represents oxyalkylene having 4 carbon atoms, and h is an average number of moles of BO added and indicates a value of 1 to 5;

(D) a polyhydric alcohol other than the (C);

(E) a silicone oil having a kinematic viscosity of 20 $mm^2$/s or less at 25° C.; and (F) water, wherein a ratio (A)/(B) of a mass of the (A) to a mass of the (B) satisfies 1.0 to 15.0 and the microemulsion composition has a transparent to translucent appearance at 25° C.

2. The microemulsion composition according to claim 1, wherein the polyether-modified organopolysiloxane (A) has an HLB of 8.0 or more and 13.0 or less calculated by Griffin's method.

3. The microemulsion composition according to claim 2, wherein the polyether-modified organopolysiloxane (A) has an HLB of 8.5 or more and 10.5 or less calculated by Griffin's method.

4. The microemulsion composition according to claim 3, wherein the polyether-modified organopolysiloxane (A) is PEG-9 Dimethicone.

5. The microemulsion composition according to claim 1, wherein the microemulsion composition is dispersible when added in water.

6. The microemulsion composition according to claim 2, wherein the microemulsion composition is dispersible when added in water.

7. The microemulsion composition according to claim 3, wherein the microemulsion composition is dispersible when added in water.

8. The microemulsion composition according to claim 4, wherein the microemulsion composition is dispersible when added in water.

9. The microemulsion composition according to claim 1, wherein 0.1 to 10 wt % of the polyether-modified organopolysiloxane (A) is contained relative to the microemulsion composition.

10. The microemulsion composition according to claim 2, wherein 0.1 to 10 wt % of the polyether-modified organopolysiloxane (A) is contained relative to the microemulsion composition.

11. The microemulsion composition according to claim 3, wherein 0.1 to 10 wt % of the polyether-modified organopolysiloxane (A) is contained relative to the microemulsion composition.

12. The microemulsion composition according to claim 4, wherein 0.1 to 10 wt % of the polyether-modified organopolysiloxane (A) is contained relative to the microemulsion composition.

13. The microemulsion composition according to claim 5, wherein 0.1 to 10 wt % of the polyether-modified organopolysiloxane (A) is contained relative to the microemulsion composition.

14. The microemulsion composition according to claim 6, wherein 0.1 to 10 wt % of the polyether-modified organopolysiloxane (A) is contained relative to the microemulsion composition.

15. The microemulsion composition according to claim 7, wherein 0.1 to 10 wt % of the polyether-modified organopolysiloxane (A) is contained relative to the microemulsion composition.

16. The microemulsion composition according to claim 8, wherein 0.1 to 10 wt % of the polyether-modified organopolysiloxane (A) is contained relative to the microemulsion composition.

17. The microemulsion composition according to claim 1, wherein the polyhydric alcohol (D) is glycerol, diglycerol or polyglycerol.

18. The microemulsion composition according to claim 2, wherein the polyhydric alcohol (D) is glycerol, diglycerol or polyglycerol.

19. The microemulsion composition according to claim 1, wherein the (E) is one or more selected from decamethylcyclopentasiloxane, dimethyl polysiloxane, or methylphenylpolysiloxane.

20. A cosmetic comprising the microemulsion composition according to claim 1.

* * * * *